US012603157B2

(12) United States Patent
Zhang et al.

(10) Patent No.: US 12,603,157 B2
(45) Date of Patent: Apr. 14, 2026

(54) METHOD AND SYSTEM FOR EVALUATING MELT FRAGMENTATION IN SODIUM-COOLED FAST REACTOR (SFR)

(71) Applicant: Xi'an Jiaotong University, Xi'an (CN)

(72) Inventors: Bin Zhang, Xi'an (CN); Wenpeng Wang, Xi'an (CN); Sheng Cao, Xi'an (CN); Minghao Hu, Xi'an (CN); Jianqiang Shan, Xi'an (CN)

(73) Assignee: Xi'an Jiaotong University, Xi'an (CN)

( * ) Notice: Subject to any disclaimer, the term of this patent is extended or adjusted under 35 U.S.C. 154(b) by 173 days.

(21) Appl. No.: 18/327,008

(22) Filed: May 31, 2023

(65) Prior Publication Data

US 2024/0312571 A1     Sep. 19, 2024

(30) Foreign Application Priority Data

May 31, 2022     (CN) .......................... 202210614657.1

(51) Int. Cl.
| | |
|---|---|
| *G01N 33/48* | (2006.01) |
| *G01N 33/50* | (2006.01) |
| *G16C 20/10* | (2019.01) |

(52) U.S. Cl.
CPC .................................... *G16C 20/10* (2019.02)

(58) Field of Classification Search
CPC ......... G16C 20/10; Y02E 30/30; G06F 30/25; G06F 30/28; G06F 2111/10; G06F 2113/08; G06F 2119/08; G06F 2119/14
See application file for complete search history.

(56) References Cited

FOREIGN PATENT DOCUMENTS

| CN | 107563030 A | 1/2018 |
|---|---|---|
| CN | 111832214 A | 10/2020 |
| CN | 113657049 A | 11/2021 |

*Primary Examiner* — Russell S Negin

(57) ABSTRACT

A method for evaluating melt fragmentation in a sodium-cooled fast reactor (SFR), in which a high-order accurate particle method is adopted to discretely solve a corresponding model and calculate the melt fragmentation process in the SFR. A least-squares moving particle semi-implicit method with high-order accuracy for gradient and Laplace models is used, and a particle-shifting technique is used to maintain a more uniform particle distribution. A geometry-based free surface identification technique is adopted. An equation-of-state model is introduced to enable acquisition of more realistic physical parameters. The solid-liquid coupling model and the phase transition model are combined to carry out the high-order accurate discretization. An evaluation system is also provided. The melt fragmentation data can be updated to the system in real time, and a real-time dynamic graph of the melt fragmentation process is automatically generated, and real-time dynamic cloud graphs of different influencing factors are automatically generated.

10 Claims, 7 Drawing Sheets

0.05s      0.1s      0.3s      0.8s      2s

| 0.05s | 0.1s | 0.3s | 0.8s | 2s |

0.05s        0.1s        0.3s        0.8s        2s

METHOD AND SYSTEM FOR EVALUATING MELT FRAGMENTATION IN SODIUM-COOLED FAST REACTOR (SFR)

CROSS-REFERENCE TO RELATED APPLICATIONS

This application claims the benefit of priority from Chinese Patent Application No. 202210614657.1, filed on May 31, 2022. The content of the aforementioned application, including any intervening amendments thereto, is incorporated herein by reference in its entirety.

TECHNICAL FIELD

This application relates to safety analysis of sodium-cooled fast reactors, and more particularly to a method and a system for evaluating melt fragmentation in a sodium-cooled fast reactor (SFR).

BACKGROUND

Molten fuel-coolant interaction (MFCI) is a major phenomenon occurring in core meltdown accidents. Many experimental and numerical simulation studies related to MFCI have been carried out at home and abroad, most of which aim at water reactors. However, considering that different coolants vary in thermal conductivity, viscosity, surface tension, density, boiling point, and observability, the MFCI of liquid metal-cooled reactors (e.g., sodium-cooled fast reactors (SFRs)) is significantly different from that of water reactors, and it has been barely reported about the melt fragmentation in SFRs in the prior art.

In terms of numerical simulation, the traditional Eulerian methods have problems in capturing the phase interface and determining the free surface for different substances in different phase states, while some traditional Lagrangian methods also suffer from low computational accuracy and relative instability. In addition, the traditional experimental methods generally adopt fragmentation phenomenon or changes in the final morphology and size of fragments to analyze the influence factors of fragmentation, and have difficulty in describing the specific fragmentation process and mechanism, and obtaining consistent simulation results and experimental results, so that they are limited in the practical application.

SUMMARY

An object of the present disclosure is to provide a method and a system for evaluating melt fragmentation in sodium-cooled fast reactors (SFRs) to overcome the deficiencies in the prior art. In this application, a high-order accurate least-square moving particle semi-implicit (LSMPS) method is utilized in combination with an improved free surface determination method, a particle shifting (PS) scheme, a fluid-fluid surface tension model, an equation of state (EOS), a solid-liquid coupling model and a phase transition model to complete numerical calculations of melt fragmentation and debris bed formation behavior in the SFRs.

The technical solutions of the present disclosure are described below.

In a first aspect, this application provides a method for evaluating melt fragmentation in sodium-cooled fast reactors, comprising:

(S1) reading and pre-processing information of each of a plurality of particles, wherein the information comprises initial position, velocity, temperature, pressure, phase, and particle bulk number;

(S2) creating a Link-list; determining distribution of the plurality of particles in a Link-list grid after the pre-processing in step (S1); searching for neighboring particles with a corresponding cutoff radius, and storing the neighboring particles; determining a free surface; optimizing the distribution of the plurality of particles using an optimized particle-shifting scheme;

(S3) according to an optimized distribution obtained in step (S2), performing discretization on a temperature discretization operator using a high-order discretization model in combination with a heat transfer and phase transition model; re-calculating temperature, enthalpy and liquid phase volume fraction of each of the plurality of particles in a computational domain according to a heat conduction equation; and updating physical parameters of the plurality of particles according to the temperature and the liquid phase volume fraction in combination with an equation of state (EOS);

(S4) smoothing density and viscosity of the plurality of particles with updated physical parameters obtained in step (S3);

(S5) calculating a viscous force of individual particles according to smoothed density and viscosity of the plurality of particles obtained in step (S4) in combination with velocity and viscosity; calculating a surface tension of the plurality of particles according to an inter-particle free energy model; making explicit correction to the velocity and a position of each of the plurality of particles based on the viscous force, the surface tension and gravity to obtain an intermediate velocity and an intermediate position of each of the plurality of particles at each time step; and (S6) solving a pressure Poisson equation according to a least-square moving particle semi-implicit (LSMPS) method to implicitly solve the pressure of each of the plurality of particles; updating the velocity and the position of each of the plurality of particles based on the pressure, and obtaining a velocity and a position of each of the plurality of particles at an $n+1^{th}$ time step in combination with the intermediate velocity and the intermediate position obtained in step (S5); searching for a particle bulk according to passively moving solid (PMS) correction to acquire center-of-gravity (CG) information of the particle bulk; updating a velocity and a position of each particle in the particle bulk according to calculated velocity and calculated angular velocity of the particle bulk, so as to complete calculation at each time step in turn, thereby generating real-time melt fragmentation data of the SFR for evaluation of fragmentation characteristics of melts in the SFR.

In some embodiments, the method further comprises:

(S7) updating generated real-time melt fragmentation data of the SFR to a system, thereby automatically generating a real-time dynamic graph of a melt fragmentation process in the SFR.

In some embodiments, in step (S7), a real-time dynamic cloud graph of results of different influencing factors is automatically generated by combining the different influencing factors.

In some embodiments, step (S2) comprises:

gridding a distribution area of the plurality of particles in a time step; traversing the plurality of particles, and recording a grid location where each particle is located, and serial numbers of particles in each grid; searching for the neighboring particles of each of the plurality of particles in a first circular region, and recording serial numbers of the neighboring particles based on the gridding in each time step; searching for neighboring particles of particle i in a second circular region, wherein the second circular region consists of a grid where the particle i is located, and surrounding grids thereof; defining a surrounding area of the particle i as a virtual screen; dividing the virtual screen into $N_v$ quadrants; determining a shadow segment of each of the neighboring particles of the particle i; and calculating the number of shadow segments of individual neighboring particles of the particle i, wherein particles with the number of shadow segments greater than $\frac{1}{6}$ are configured as free surface particles.

In some embodiments, in step (S2), the optimized particle shifting-optimizing scheme is expressed by:

$$\delta \vec{r}_i = -\lambda_{shift}(\Delta l)^2 (\nabla D_i - (\vec{n}_i \cdot \nabla D_i)\vec{n}_i) = -\lambda_{shift}(\Delta l)^2 (\vec{I} - \vec{n}_i \otimes \vec{n}_i)\nabla D_i;$$

wherein $\delta \vec{r}_i$; represents a corrected displacement; $\lambda_{shift}$ represents a constant parameter; $\Delta l$ represents an initial distance between particles; D represents a diffusion concentration; and $\vec{n}_i$ represents a corrected unit vector.

In some embodiments, step (S3) is performed through steps of:

(S301) performing the discretization on the temperature discretization operator using the LSMPS method; calculating an internal energy of each of the plurality of particles in each time step; and calculating a temperature and an enthalpy of each of the plurality of particles in a $k+1^{th}$ time step;

(S302) after calculating the enthalpy of each of the plurality of particles in step (S301), separately calculating the liquid phase volume fraction $\alpha$ and the temperature T of particles of different substances; and (S303) according to enthalpy h and temperature T obtained in each time step, updating the physical parameters of each of the plurality of particles in combination with an equation of state (EOS) model, wherein the EOS model is expressed as:

$$T_{Sm} = T_{Sol} + \frac{T_{Liq} - T_{Sol}}{h_f}(e_{Sm} - e_{Sol});$$

wherein $e_{Sol} < e_{Sm} < e_{Liq}$; $T_{Sm}$ represents a temperature of incompressible particles; $e_{Sol}$ represents a solidus energy; $e_{Sm}$ represents internal energy; and $h_f$ represents enthalpy.

In some embodiments, in step (S301), the temperature $T_i^{k+1}$ and the enthalpy $h_i^{k+1}$ of each of the plurality of particles in the $k+1^{th}$ time step are respectively expressed as:

$$T_i^{k+1} = T_i^k + \frac{\Delta t}{\rho C_P}\frac{2}{n_0}\sum_{j \neq i}\left\{k_{ij}(T_j^k - T_i^k)w_{ij}\frac{[C_3 + C_4]P}{r_{ij}l_0}\right\} \text{ and};$$

$$h_i^{k+1} = h_i^k + \frac{\Delta t}{\rho}\frac{2}{n_0}\sum_{j \neq i}\left\{k_{ij}(T_j^k - T_i^k)w_{ij}\frac{[C_3 + C_4]P}{r_{ij}l_0}\right\};$$

wherein $T_i^k$ represents a particle temperature within a $k^{th}$ time step; $\Delta t$ represents time step; $\rho$ represents density; $C_P$ represents constant-pressure specific heat; $n_0$ represents number density; $k_{ij}$ represents a thermal-conductivity coefficient; $T_j^k$ represents temperature; $w_{ij}$ represents a kernel function; $r_{ij}$ represents an interparticle distance; $l_0$ represents particle diameter; $C_3 + C_4$ represents a correction matrix in the LSMPS; P represents a relative position vector; and $h_i^k$ is a particle enthalpy within the $k^{th}$ time step.

In some embodiments, in step (S302), the liquid phase volume fraction $\alpha$ and the temperature T of each of the plurality of particles are respectively expressed as:

$$\begin{cases} \alpha_i = 0, h_i \leq h_s \\ \alpha_i = \frac{h_i - h_s}{h_l - h_s}, h_l < h_i < h_s \\ \alpha_i = 1, h_i \geq h_l \end{cases} \text{; and}$$

$$\begin{cases} T_i = T_m + \frac{h_i - h_s}{\rho c}, h_i \leq h_s \\ T_i = T_m, h_l < h_i < h_s \\ T_i = T_m + \frac{h_i - h_l}{\rho c}, h_i \geq h_l \end{cases};$$

wherein $\alpha_i$ represents a liquid phase volume fraction of particle i; $h_i$ represents an enthalpy of the particle i; $h_s$ represents a melting enthalpy of a solid particle; $h_l$ represents a solidification enthalpy of a liquid particle; $T_i$ represents a temperature of the particle i; $T_m$ represents a particle melting point; $\rho$ represents density; and c represents specific heat capacity.

In some embodiments, in step (S5), a new momentum conservation equation is expressed as:

$$\frac{D\vec{u}}{Dt} = -\frac{\nabla p}{\rho} + \frac{1}{\rho}\nabla \cdot (\hat{\mu}\nabla \vec{u}) + \vec{g} + \frac{\vec{f}_s}{\rho};$$

wherein $D\vec{u}$ represents a total derivative with respect to velocity; Dt represents a total derivative with respect to time; $\nabla p$ represents a pressure gradient; $\nabla \vec{u}$ represents a velocity gradient; $\vec{g}$ represents gravity; $\vec{f}_s$ represents an additional force other than gravity; and $\rho$ represents density.

In some embodiments, in step (S5), the intermediate velocity and the intermediate position of each of the plurality of particles in each time step are respectively expressed as:

$$\vec{u}^* = \vec{u}^n + \Delta t\left(\frac{1}{\rho}\nabla \hat{\mu} \cdot \nabla \vec{u}^n + \frac{\hat{\mu}}{\rho}\nabla^2 \vec{u}^n + \vec{g} + \vec{f}^n\right); \text{ and}$$

$$\vec{r}^* = \vec{r}^n + \Delta t\vec{u}^*;$$

wherein $\vec{u}^n$ represents a velocity in an $n^{th}$ time step; $\Delta t$ represents a calculated time step size; $\nabla \hat{u}$ represents a viscosity gradient after smoothed; $\nabla \vec{u}^n$ represents a velocity gradient in the $n^{th}$ time step; $\vec{g}$ represents gravity; and $\vec{f}^n$ represents a surface tension in the $n^{th}$ time step.

In some embodiments, in step (S6), the velocity and the position of each of the plurality of particles in the $n+1^{th}$ time step are respectively expressed as:

$$p^{n+1} = p^{**};$$

$$\vec{u}^{n+1} = \vec{u}^* - \Delta t \frac{1}{\hat{\rho}} \nabla p^{n+1};$$

$$\vec{r}^{n+1} = \vec{r}^n + \nabla \vec{m}^{n+1};$$

$$\vec{r}_i^{n+1} = \vec{r}_i^n + M(\vec{r}_i^n - \vec{r}_{c,ii}^n); \text{ and}$$

$$\vec{u}_i^{n+1} = \frac{(\vec{r}_i^{n+1} - \vec{r}_i^n)}{\Delta t};$$

wherein $p^{n+1}$ represents a pressure in the $n+1^{th}$ time step; $\vec{u}^{n+1}$ represents a velocity in the $n+1^{th}$ time step; $\vec{u}*$ represents the intermediate velocity; $\Delta t$ represents time step; $\hat{\rho}$ represents a smoothed density; $\nabla p^{n+1}$ represents a pressure gradient in the $n+1^{th}$ time step; $\vec{r}^{n+1}$ represents a displacement in the $n+1^{th}$ time step; $\vec{r}^n$ represents a displacement in an $n^{th}$ step; $\vec{r}^{n+1}$ represents a displacement of particle i in the $n+1^{th}$ time step; M represents a coordinate transformation matrix; and $\vec{r}_{c,ii}^n$ represents a displacement of a solid block in the $n^{th}$ time step.

In a second aspect, this application provides system for evaluating melt fragmentation in a sodium-cooled fast reactor, comprising:

a reading module;

an optimizing module;

an updating module;

a processing module;

a correcting module; and an analyzing module;

wherein the reading module is configured to read and pre-process information of each of a plurality of particles, wherein the information comprises initial position, velocity, temperature, pressure, phase, and particle bulk number information;

the optimizing module is configured to create a Link-list, determine distribution of the plurality of particles in a Link-list grid after pre-processed by the reading module, search for neighboring particles with a corresponding cutoff radius, store the neighboring particles, determine a free surface, and optimize the distribution of the plurality of particles using an optimized particle-shifting scheme;

the updating module is configured to perform discretization on a temperature discretization operator using a high-order discretization model according to an optimized distribution obtained by the optimizing module combined with a heat transfer and phase transition model, re-calculate temperature, enthalpy and liquid phase volume fraction of each of the plurality of particles in a computational domain according to a heat conduction equation, and update physical parameters of the plurality of particles according to the temperature and the liquid phase volume fraction in combination with an equation of state (EOS);

the processing module is configured to smooth density and viscosity of the plurality of particles with updated physical parameters;

the correcting module is configured to calculate a viscous force of individual particles according to smoothed density and viscosity of the plurality of particles obtained by the processing module, calculate a surface tension of the plurality of particles according to an inter-particle free energy model, make explicit correction to the velocity and a position of each of the plurality of particles based on the viscous force, the surface tension and gravity to obtain an intermediate velocity and an intermediate position of each of the plurality of particles at each time step; and the analyzing module is configured to solve a pressure Poisson equation according to a LSMPS method to implicitly solve the pressure of each of the plurality of particles, update the velocity and the position of each of the plurality of particles based on the pressure and obtain a velocity and a position of each of the plurality of particles at an $n+1^{th}$ time step in combination with the intermediate velocity and the position obtained by the correcting module, search for a particle bulk according to PMS correction to acquire center of gravity (CG) information of the particle bulk, and update a velocity and a position of each particle in the particle bulk according to a calculated velocity and a calculated angular velocity of the particle bulk, so as to complete calculation at each time step in turn, thereby generating real-time melt fragmentation data of the sodium-cooled fast reactor for evaluation of fragmentation characteristics of melts in the sodium-cooled fast reactor.

The method for evaluating melt fragmentation of a sodium-cooled fast reactor disclosed herein adopts the LSMPS method which has higher order accuracy for both gradient model and Laplace model, and in the meanwhile, the particle shifting technology is used to keep the particles being distributed more uniformly during calculation, and combined with the free surface identification technology based on the geometric method to allow for a higher stability of the Lagrange particles during calculation, thereby obtaining calculation results with higher accuracy. By using the optimized particle shifting scheme, the distribution of particles is more uniform during calculation, thus reducing their instability. At the same time, the equation of state is used to obtain the physical properties of the particles, which is closer to the real physical property parameters. By using the LSMPS method, and the high-order precision discrete operator is used to improve the overall computation accuracy. Furthermore, to describe the free surface particles more accurate, this geometric feature-based detection method is adopted, and it is verified through multiple calculations that when the number of shaded segments is greater than ⅙, the description of the free surface particles is more accurate and more adaptable to the calculation results. The LSMPS method can guarantee a high computational accuracy. However, the computational accuracy is very sensitive to the particle distribution. Particularly, particles distributed sparsely may lead to decreased computational accuracy, while particles distributed tightly can lead to numerical instability. If the particles move in a full Lagrangian manner, the particles will be highly concentrated along the streamline over time. The distribution of highly-anisotropic particles can lead to numerical instability or large errors, and even if a consistent discrete format is used. In such cases, long-time simulations are actually required, and the errors accumulated at each time step cannot be ignored. Therefore, the optimized particle shifting technique is used herein to ensure that the particles move slightly at each time step to maintain a uniform distance between particles and improve computational stability.

Further, through the calculation of the energy at each time step, the enthalpy and temperature of the particles at each time step are obtained. By combining with the equation of state, the physical property parameters of each particle that are closer to the real working conditions are calculated, and the physical properties of different reactor materials can be obtained through the physical property parameter function database.

The iterative calculation of temperature and enthalpy by using the LSMPS high-order precision discrete operator makes the calculation accuracy substantially improved compared with the traditional MPS method.

By using the method provided herein, the physical state of the particles at each time step can be obtained, so that the phase state, temperature, share and other physical parameters of the particles at this time can be obtained more accurately.

In solid-liquid mixed flow and the gas-liquid mixed flow, large sudden changes in density and viscosity always occur. To alleviate the numerical difficulties caused by such sudden changes, the density and viscosity coefficients of the particles are smoothed in a certain region in this application. The smoothing treatment of the momentum conservation equation makes the calculation more stable. Further, the pressure of the particles is solved implicitly. Then, the velocity and position of the particles are updated using the pressure to obtain the velocity and position at an $n+1^{th}$ time step.

In summary, this application combines the advantages of the Lagrangian method while using the high-order precision particle method and related models to provide a method for evaluating melt fragmentation in a sodium-cooled fast reactor.

The technical solutions of the present disclosure will be described in further detail below with reference to the accompanying drawings and embodiments.

DETAILED DESCRIPTION OF EMBODIMENTS

Figure 1:
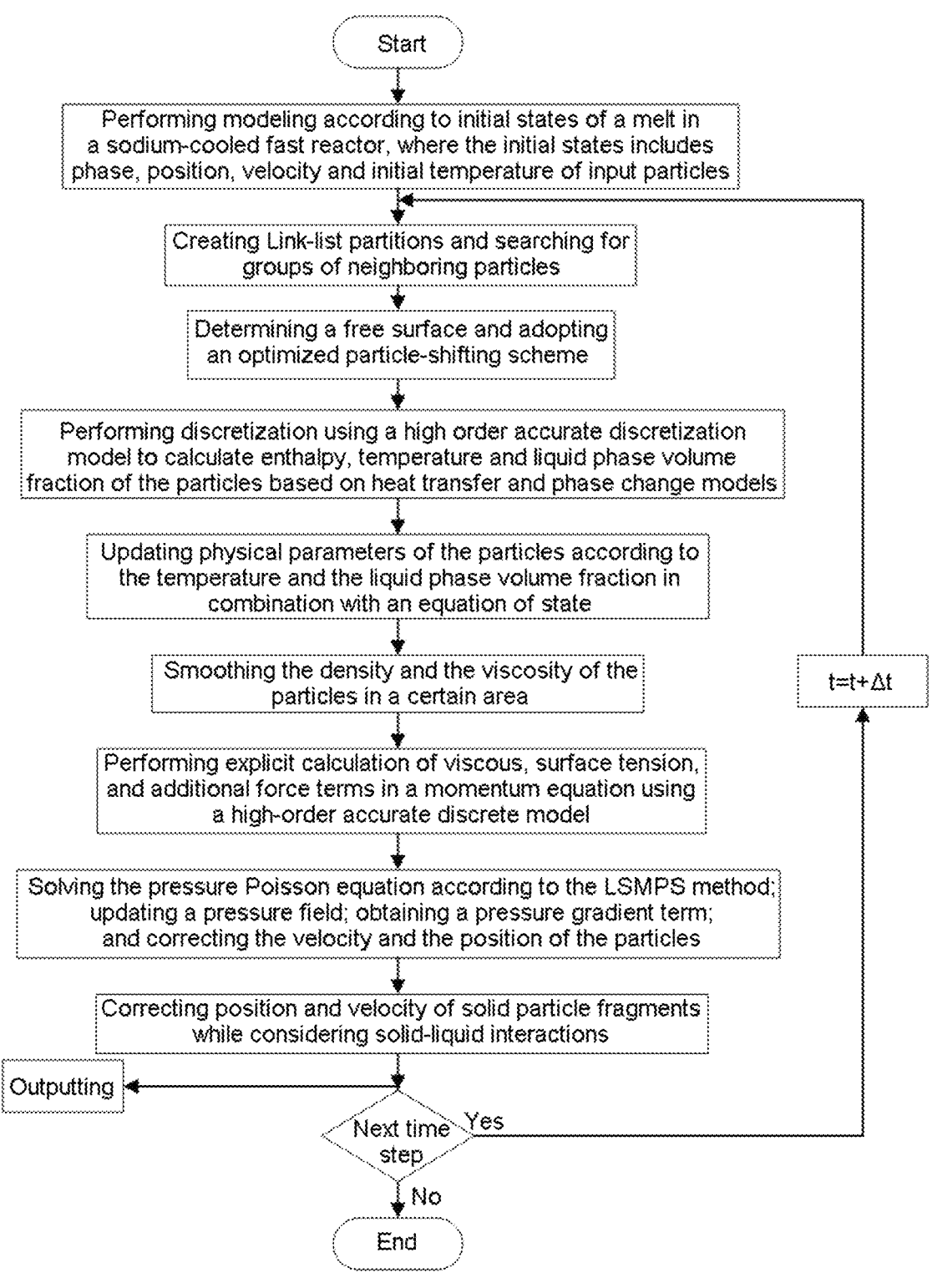
FIG. 1 is a flow chart of a method for evaluating melt fragmentation in a sodium-cooled fast reactor according to an embodiment of the present disclosure.

The technical solutions of the present disclosure will be clearly and completely described below with reference to the accompanying drawings. Obviously, the described embodiments are a part of the embodiments of the present disclosure. Based on these embodiments, all other embodiments made by one of ordinary skill in the art without creative labor shall fall within the scope of protection of the present disclosure.

In the description of the present disclosure, it should be understood that the terms "including" and "comprising" indicate the presence of the described features, wholes, steps, operations, elements and/or components, but do not exclude the presence of one or more other features, wholes, steps, operations, elements, components and/or combinations thereof.

It should also be understood that the terms used herein are merely used for describing particular embodiments, rather than limiting the present disclosure. As used in the specification and the appended claims, unless clearly otherwise, the singular forms "one", "a" and "the" are intended to include the plural form.

It also should be understood that the term "and/or" as used in the specification and the appended claims refers to all possible combination of one or more of the items listed in association. For example, "A and/or B" may refers to A alone, both A and B, or B alone. In addition, the character "/" herein generally indicates an "or" relationship between associated objects.

It should be understood that although the terms "first", "second" and "third" may be used in embodiments to describe the predetermined ranges, these predetermined ranges should not be limited to these terms. These terms are merely used to distinguish the predetermined ranges from one another. For example, without departing from the scope of embodiments of the present disclosure, a first predetermined range may also be referred to as a second predetermined range. Similarly, a second predetermined range may also be referred to as a first predetermined range.

As used herein, the word "if", may be interpreted as "at the time of . . . " or "when . . . " or "in response to the determination" or "in response to the detection". Similarly, the phrase "if determining" or "if detecting (the stated condition or event)" may be interpreted as "when determining", or "in response to the determination", or "when detecting (the stated condition or event)", or "in response to detecting (the stated condition or event)".

Various structural diagrams according to disclosed embodiments of the present disclosure are shown in the accompanying drawings. These drawings are not made in scale, in which some details may be enlarged, and some details may be absent for the purpose of clear illustration. The shapes of various regions and layers and their relative sizes and positional relationships shown in the drawings are merely exemplary, and may deviate due to manufacturing tolerances or technical limitations in practice. Moreover, one of ordinary skill in the art may additionally design regions/layers having different shapes, sizes, and relative positions according to the actual needs.

The present disclosure provides a method for evaluating melt fragmentation in a sodium-cooled fast reactor, in which the corresponding model is discretely solved using a high-order accuracy particle method to calculate the melt fragmentation process in the sodium-cooled fast reactor. In this method, the least squares moving semi-implicit particle (LSMPS) method that has high order accuracy for both the gradient model and the Laplace model is used, while the particle shifting (PS) technique is used to maintain a more uniform distribution of particles during computation. By combining with the free surface identification technique based on the geometrical method, the Lagrangian particles are more stable during computation, thud obtaining more highly-accurate computational results. Moreover, the equation of state model is introduced to obtain more realistic physical parameters in the calculation process. Combined with the solid-liquid coupling model and the phase transition model, the discretization is carried out with high order accuracy. Finally, the information of melt fragmentation process of the sodium-cooled fast reactor is obtained and analyzed.

As shown in FIG. 1, a method for evaluating melt fragmentation in a sodium-cooled fast reactor (SFR) is provided, which includes the following steps.

(S1) Information of each of a plurality of particles is read in from an input file, where the information includes initial position, velocity, temperature, pressure, phase, and particle bulk number. Computational parameters are set, including a truncation radius and a time step.

(S2) A Link-list algorithm is invoked every time step or several time steps to obtain distribution of the plurality of particles in a grid, which can reduce the search calculation amount for neighboring particles. After that, neighboring particles are found with a corresponding cutoff radius and then stored. A free surface is determined, and an optimized particle-shifting scheme is adopted.

Figure 2:
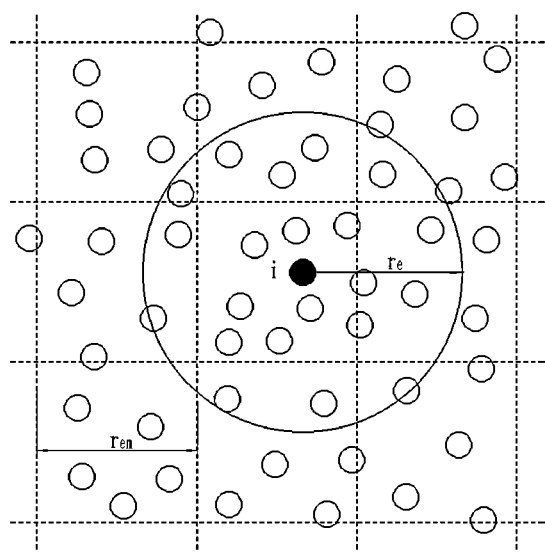
FIG. 2 schematically shows a Link-list search method according to an embodiment of the present disclosure.

Referring to FIG. 2, a Link-list algorithm is adopted herein, which can greatly reduce the time for searching. The distribution area of the particles is gridded in certain time steps, and then all the particles are traversed once to record a grid location where each particle is located and serial numbers of each particle in each grid. Since the search areas for the particles are all circular, the search for particles in circular areas is performed once more in the grid in each calculating step, and serial numbers of particles around each particle are recorded. In the second circular region search, only the grid where particle i is located and its surrounding grid are searched. The number of grids to be searched is 9 in the two-dimensional (2D) case and 27 in the three-dimensional (3D) case.

Meanwhile, a geometric feature-based detection method is used to detect the free surface particles more accurately. In the geometric model, the center of a detected particle is defined as a light source, and the surroundings of the detected particle is defined as a virtual screen. The virtual screen is divided into $N_v$ quadrants, then the shadow segment of a neighboring particle can be found through a shadow angle calculated by:

$$\theta_j = \left(\frac{180}{\pi}\right)\tan^{-1}\left(\frac{y_{ij}}{x_{ij}}\right);$$

The shadow segments of the neighboring particles are calculated by:

$$\psi = 1 - \frac{N_s}{N_v};$$

where $N_s$ represents the total number of shadow segments of the neighboring particles, and the particles are determined as the free surface particles when $\psi > \frac{1}{6}$.

At the same time, the optimized particle-shifting technique is used to avoid the uneven distribution of some Lagrangian particles in the calculation process, which is calculated as follows:

$$\delta\vec{r}_i = -\lambda_{shift}(\Delta l)^2(\nabla D_i - (\vec{n}_i \cdot \nabla D_i)\vec{n}_i) = -\lambda_{shift}(\Delta l)^2(\vec{I} - \vec{n}_i \otimes \vec{n}_i)\nabla D_i;$$

where $\lambda_{shift}$ represents a constant parameter; $\Delta l$ represents an initial interparticle; D is defined as a diffusion concentration, defined as $D_i = \Sigma V_j w(|\vec{r}_{ij}|)$; and $\vec{n}_i$ represents a modified unit vector, defined as $$\vec{n}_i = -\frac{C_i \cdot \nabla D_i}{|C_i \cdot \nabla D_i|},$$

where C represents a correction matrix.

(S3) Discretization is performed on a temperature discretization operator using a high-order accuracy discretization model according to an optimized distribution obtained in step (S2) in combination with a heat transfer and phase transition model. Temperature, enthalpy and liquid phase volume fraction of each of the plurality of particles are re-calculated according to a heat conduction equation to determine whether the phase transition occurs. Physical property parameters of the particles are updated according to the temperature and the liquid phase volume fraction in combination with an equation of state (EOS).

In the particle method, the energy transfer and temperature calculation between individual particles are achieved by thermal conductivity between neighboring particles, and the melting and solidification processes are calculated from the internal energy of the particles. The parameters, such as temperature, enthalpy, specific heat capacity, share of phase change, are stored in each particle. The thermal conductivity between the particles is calculated by the differential equation of thermal conductivity, as shown below:

$$\rho c \frac{\partial T}{\partial t} = k\nabla^2 T + Q;$$

where C represents specific heat capacity; T represents a temperature; k represents a thermal conductivity coefficient; and Q represents a volumetric heat source.

(S301) The discretization is performed on the temperature discretization operator using the LSMPS method. An internal energy of each of the plurality of particles is calculated in each time step. A temperature and an enthalpy of each of the plurality of particles in a k+1$^{th}$ time step are respectively calculated by:

$$T_i^{k+1} = T_i^k + \frac{\Delta t}{\rho C_P}\frac{2}{n_0}\sum_{j\neq i}\left\{k_{ij}(T_j^k - T_i^k)w_{ij}\frac{[C_3 + C_4]P}{r_{ij}l_0}\right\} \text{ and;}$$

$$h_i^{k+1} = h_i^k + \frac{\Delta t}{\rho}\frac{2}{n_0}\sum_{j\neq i}\left\{k_{ij}(T_j^k - T_i^k)w_{ij}\frac{[C_3 + C_4]P}{r_{ij}l_0}\right\};$$

where $T_i^k$ represents a particle temperature within a k$^{th}$ time step; $\Delta t$ represents time step; $\rho$ represents density; $C_P$ represents constant-pressure specific heat; $n_0$ represents number density; $k_{ij}$ represents a thermal-conductivity coefficient; $T_j^k$ represents temperature; $w_{ij}$ represents a kernel function; $r_{ij}$ represents an interparticle distance; $l_0$ represents particle diameter; $C_3 + C_4$ represents a correction matrix in the LSMPS; P represents a relative position vector; and $h_i^k$ is a particle enthalpy within the k$^{th}$ time step.

(S302) After calculating the enthalpy of each of the plurality of particles in each time step, the liquid phase volume fraction $\alpha$ and the temperature T of each of the particles are separately calculated by:

$$\begin{cases} \alpha_i = 0, \, h_i \leq h_s \\ \alpha_i = \frac{h_i - h_s}{h_l - h_s}, \, h_l < h_i < h_s \, ; \text{ and} \\ \alpha_i = 1, \, h_i \geq h_l \end{cases}$$

-continued $$\begin{cases} T_i = T_m + \dfrac{h_i - h_s}{\rho c}, \; h_i \le h_s \\ T_i = T_m, \; h_l < h_i < h_s \quad ; \\ T_i = T_m + \dfrac{h_i - h_l}{\rho c}, \; h_i \ge h_l \end{cases}$$

where $\alpha_i$ represents a liquid phase volume fraction of particle i; $h_i$ represents an enthalpy of the particle i; $h_s$ represents a melting enthalpy of a solid particle; $h_l$ represents a solidification enthalpy of a liquid particle; $T_i$ represents a temperature of the particle i; $T_m$ represents a particle melting point; $\rho$ represents density; and c represents specific heat capacity.

(S303) The EOS model introduced herein is to make the physical properties more accurate during the melt fragmentation in the sodium-cooled fast reactor, which is important for the accuracy, stability and computational validity of the calculations from the numerical view.

The EOS model contains the basic reactor core materials, including mixed oxide fuel (MOX), stainless steel, and sodium. These materials are assumed to be immiscible so that each material can be defined with a unique EOS.

In this case, the EOS aims at the material components and solid particles in the flow field, which is assumed to be a multinomial relation between the temperature $T_{Sm}$ and internal energy $e_{Sm}$ of incompressible particles, as shown below:

$$T_{Sm} = T_{Sol}\left[1 - \alpha_{S1}(1 - u_{Sm}) - \alpha_{S2}(1 - u_{Sm})^2 - \alpha_{S2}(1 - u_{Sm})^3\right],$$

$$(e_{Sm} < e_{Sol}); \text{ and}$$

$$T_{Sm} = T_{Sol} + \frac{T_{Liq} - T_{Sol}}{h_f}(e_{Sm} - e_{Sol}), \; (e_{Sol} < e_{Sm} < e_{Liq});$$

where $T_{Sm}$ represents a temperature of the incompressible particles; $\alpha_{S1}$, $\alpha_{S2}$ and $\alpha_{S3}$ are adjustable constants; $e_{Sol}$ represents a solidus energy; $e_{Liq}$ represents a liquid energy; $e_{Sm}$ represents the internal energy; $u_{Sm}$ is a ratio of the internal energy to the solidus energy; and $h_f$ represents an enthalpy.

The temperature $T_{Sm}$ of the incompressible particles is obtained from the multinomial equation of the internal energy $e_{Sm}$, and thermal conductivity of the solids and the liquid, and viscosity, surface tension and thermal melting of the liquid are obtained from the temperature $T_{Sm}$ and the property parameter database.

(S4) Density and viscosity of the plurality of particles are smoothed to alleviate numerical instability in pressure calculations.

In solid-liquid mixed flow and gas-liquid mixed flow, large sudden changes in density and viscosity always occurs. To alleviate the numerical difficulties brought about by such sudden changes, the density and the viscosity coefficient will be smoothed in a certain region during calculations in this application. For a fluid particle i, its density and kinetic viscosity coefficient will be weighted and averaged according to the neighboring particles, which is calculated as follows:

$$\hat{\rho} = \frac{\sum\limits_{j=1,N} \rho_j \hat{W}_{ij}}{\sum\limits_{j=1,N} \hat{W}_{ij}}; \text{ and}$$

-continued $$\hat{\mu} = \frac{\sum\limits_{j=1,N} \mu_j \hat{W}_{ij}}{\sum\limits_{j=1,N} \hat{W}_{ij}};$$

where $\hat{\rho}$ and $\hat{\mu}$ are the density and the kinetic viscosity coefficients of the particle i after smooth treatment, respectively; and $\hat{w}_{ij}$ represents the kernel function adopted in the smooth treatment, as shown below:

$$\hat{W}_{ij} = \alpha_d \begin{cases} \dfrac{2}{3} - \left(\dfrac{|\vec{r}_{ij}|}{r_e}\right)^2 + \dfrac{1}{2}\left(\dfrac{|\vec{r}_{ij}|}{r_e}\right)^3, \; 0 \le \dfrac{|\vec{r}_{ij}|}{r_e} < 0.5 \\ \dfrac{1}{6}\left(2 - \dfrac{|\vec{r}_{ij}|}{r_e}\right)^3, \; 0.5 \le \dfrac{|\vec{r}_{ij}|}{r_e} < 1 \quad ; \\ 0, \text{ else} \end{cases}$$

where the coefficient $\alpha_d$ is $$\frac{2}{r_e}, \; \frac{60}{7\pi r_e^2} \text{ and } \frac{12}{\pi r_e^3}$$

in one-dimensional (1D), two-dimensional (2D) and three-dimensional (3D) conditions, respectively; and the truncation radius in the smoothing treatment is set as $r_e = 4.1\Delta l$.

The density and the kinetic viscosity coefficient are smoothed to obtain a new conservation-of-momentum equation, shown as:

$$\frac{D\vec{u}}{Dt} = -\frac{\nabla p}{\hat{\rho}} + \frac{1}{\hat{\rho}}\nabla \cdot (\hat{\mu}\nabla\vec{u}) + \vec{g} + \frac{\vec{f}_s}{\rho};$$

where $D\vec{u}$ represents a total derivative with respect to velocity; Dt represents a total derivative with respect to time; $\nabla p$ represents a pressure gradient; $\nabla \vec{u}$ represents a velocity gradient; $\vec{g}$ represents gravity; $\vec{f}_s$ represents an additional force other than gravity; and $\rho$ represents density.

(S5) A high-order accuracy discrete model is used to calculate the viscous, surface tension, and extra force terms in the momentum equation.

Viscous forces are calculated based on the velocity and the viscosity, and the surface tension is calculated based on a surface free energy model.

In the case of considering the simulation of interfacial tension between the fluids during the interaction between the melt and the coolant, the surface tension coefficients between two different fluids 1 and 2 are taken into account, shown as:

$$\sigma_{12} = \sigma_1 + \sigma_2 - 2\Phi\sqrt{\sigma_1\sigma_2};$$

where $$\Phi = \frac{4(V_1 V_2)^{1/3}}{\left(V_1^{1/3} + V_2^{1/3}\right)^2};$$

V is a molar volume of the corresponding fluid.

The resulting surface tension parameter $C_{12}$ between the two different fluids is calculated by:

$$C_{12} = \frac{2\Delta l^2}{\sum_{i \in A, j \in B} e(r)} \Phi \sqrt{\sigma_1 \sigma_2};$$

where $\Delta l$ represents an initial interparticle distance; $e(r)$ represents the free energy; $\sigma_1$ is a surface tension coefficient of the fluid 1; $\sigma_2$ is a surface tension coefficient of the fluid 2; A represents particle i; and B represents particle j.

The surface tension parameter $C_{12}$ between the two different fluids is brought into the free energy model, so that the surface tension action at the interface between the two different fluids can be obtained through the fluid surface tension calculation.

At the same time, explicit corrections are carried out on the velocity and the position using the viscous forces, the surface tension and gravity to obtain an intermediate velocity and an intermediate position of each of the plurality of particles in each time step, expressed as:

$$\vec{u}^* = \vec{u}^n + \Delta t \left( \frac{1}{\rho} \nabla \hat{\mu} \cdot \nabla \vec{u}^n + \frac{\hat{\mu}}{\rho} \nabla^2 \nabla \vec{u}^n + \vec{g} + \vec{f}^n \right); \text{ and}$$

$$\vec{r}^* = \vec{r}^n + \Delta t \vec{u}^*;$$

where $\vec{u}^n$ represents a velocity in an $n^{th}$ time step; $\Delta t$ represents a calculated time step size; $\nabla \hat{\mu}$ represents a viscosity gradient after smoothed; $\nabla \vec{u}^n$ represents a velocity gradient in the $n^{th}$ time step; $\vec{g}$ represents gravity; and $\vec{f}^n$ represents a surface tension in the $n^{th}$ time step.

(S6) A pressure Poisson equation is solved according to a least-square moving particle semi-implicit (LSMPS) method to implicitly solve the pressure of each of the plurality of particles. Then the velocity and the position of each of the plurality of particles are updated based on the pressure to obtain a velocity and a position of each of the plurality of particles at an $n+1^{th}$ time step. A particle bulk is searched according to PMS correction to acquire center-of-gravity (CG) information of the particle bulk. A velocity and a position of each particle in the particle bulk are updated according to calculated velocity and calculated angular velocity of the particle bulk, so as to complete calculation at each time step in turn, thereby obtaining information within the melt fragmentation computational domain to support subsequent melt fragmentation analysis for the SFR.

The velocity and the position of each of the plurality of particles at an $n+1^{th}$ time step are respectively expressed as:

$$p^{n+1} = p^{**};$$

$$\vec{u}^{n+1} = \vec{u}^* - \Delta t \frac{1}{\hat{\rho}} \nabla p^{n+1};$$

$$\vec{r}^{n+1} = \vec{r}^n + \Delta t \vec{u}^{n+1};$$

$$\vec{r}_i^{n+1} = \vec{r}_i^n + M\left(\vec{r}_i^n - \vec{r}_{c,ii}^n\right); \text{ and}$$

$$\vec{u}_i^{n+1} = \frac{\left(\vec{r}_i^{n+1} - \vec{r}_i^n\right)}{\Delta t};$$

where $p^{n+1}$ represents a pressure in the $n+1^{th}$ time step; $\vec{u}^{n+1}$ represents a velocity in the $n+1^{th}$ time step; $\vec{u}*$ represents the intermediate velocity; $\Delta t$ represents time step; $\rho$ represents a smoothed density; $\nabla p^{n+1}$ represents a pressure gradient in the $n+1^{th}$ time step; $\vec{r}^{n+1}$ represents a displacement in the $n+1^{th}$ time step; $\vec{r}^n$ represents a displacement in an $n^{th}$ step; $\vec{r}_i^{n+1}$ represents a displacement of particle i in the $n+1^{th}$ time step; M represents a coordinate transformation matrix; and $\vec{r}_{c,ii}^n$ represents a displacement of a solid block in the $n^{th}$ time step.

By adding an EOS database, changes in the physical property parameters of the fuel melt and the coolant sodium over temperature can be automatically updated in real time, and the generated physical property parameters can be updated to the physical property parameter database of different substances. The present disclosure can automatically identify the number of fragments and classify the fragment size, dynamically output the changes in the number of fragments under different influencing factors at different moments, and update the fragment size database, so that the database is continuously updated and expanded.

Figure 4A:
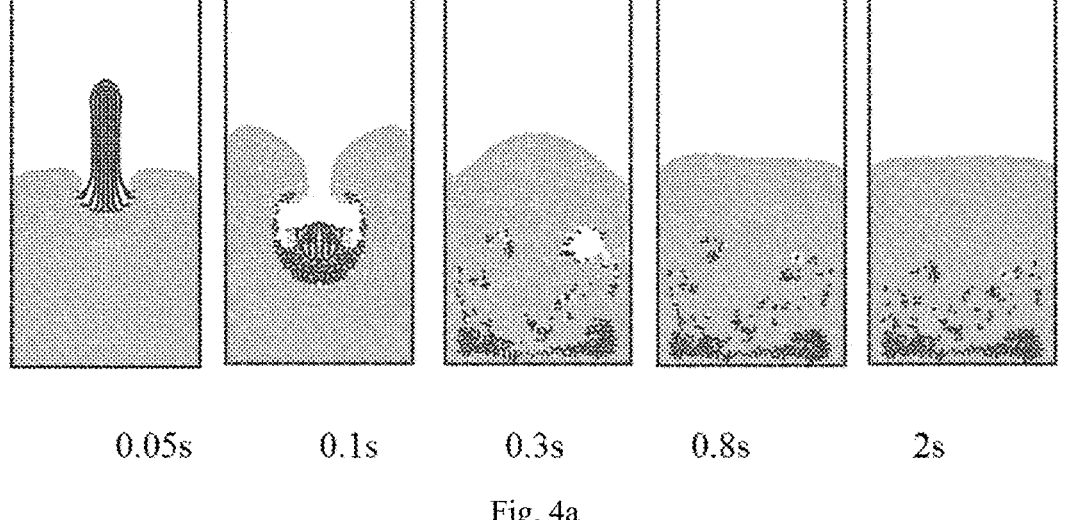
FIGS. 4 (*a*)-(*c*) are respectively real-time dynamic plots of melt position distribution, debris formation process, and temperature distribution according to an embodiment of the present disclosure.
Figure 4B:
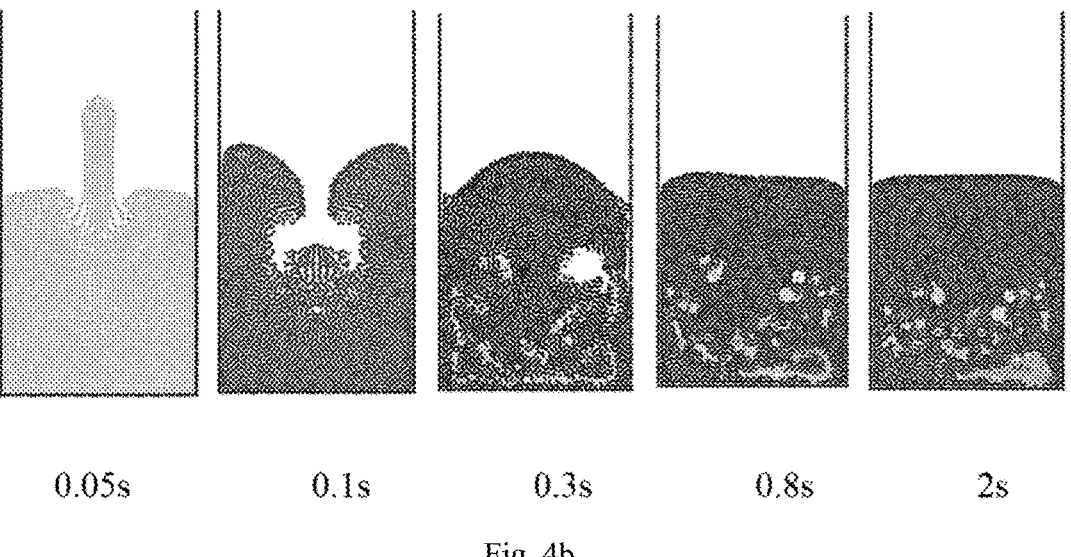
Figure 4C:
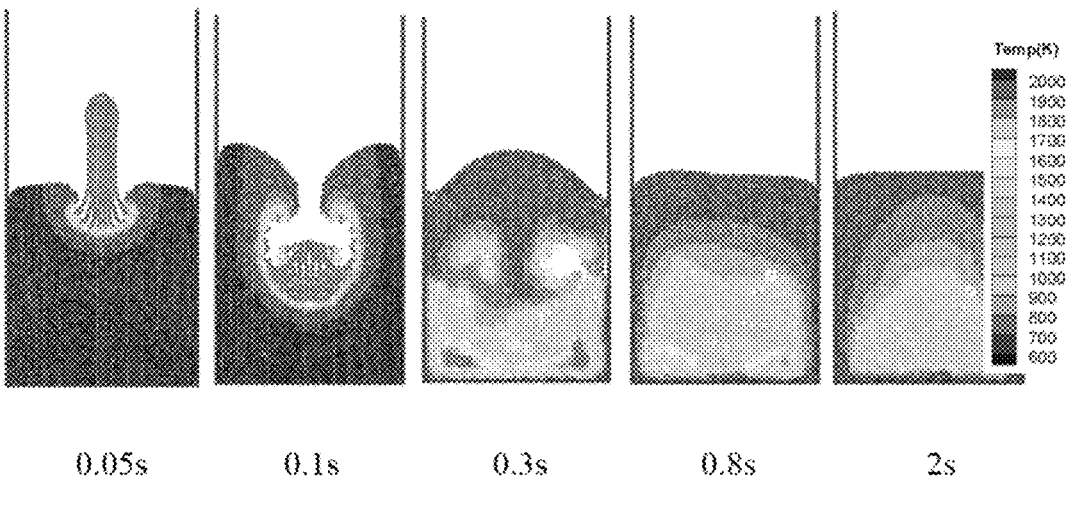

The real-time generated melt fragmentation data in the sodium-cooled fast reactor is updated to the system, which then automatically generates a real-time dynamic graph of the melt fragmentation process, and automatically generates a real-time dynamic cloud graph of the results of different influencing factors (temperature, melt distribution, and debris distribution) in combination with the different influencing factors, as shown in FIGS. 4(a)-(c) in some embodiments.

This application also provides a system for evaluating melt fragmentation in a sodium-cooled fast reactor, which can implement the aforementioned method for evaluating melt fragmentation in the sodium-cooled fast reactor. Specifically, the system includes a reading module, an optimizing module, an updating module, a processing module, a correcting module, and an analyzing module.

The reading module is configured to read and pre-process information of each of a plurality of particles, wherein the information comprises initial position, velocity, temperature, pressure, phase, and particle bulk number information.

The optimizing module is configured to create a Link-list partition, determine distribution of the plurality of particles in a Link-list grid after pre-processed by the reading module, search for neighboring particles with a corresponding cutoff radius, store the neighboring particles, determine a free surface, and optimize the distribution of the plurality of particles using an optimized particle-shifting scheme.

The updating module is configured to perform discretization on a temperature discretization operator using a high-order discretization model according to an optimized distribution obtained by the optimizing module combined with a heat transfer and phase transition model, re-calculate temperature, enthalpy and liquid phase volume fraction of each of the plurality of particles in a computational domain according to a heat conduction equation, and update physical parameters of the plurality of particles according to the temperature and the liquid phase volume fraction in combination with an EOS.

The processing module is configured to smooth density and viscosity of the plurality of particles with updated physical parameters.

The correcting module is configured to calculate a viscous force of individual particles according to smoothed density and viscosity of the plurality of particles obtained by the processing module, calculate a surface tension of the plurality of particles according to an inter-particle free energy model, make explicit correction to the velocity and a position of each of the plurality of particles based on the viscous force, the surface tension and gravity to obtain an intermediate velocity and an intermediate position of each of the plurality of particles at each time step.

The analyzing module is configured to solve a pressure Poisson equation according to a LSMPS method to implicitly solve the pressure of each of the plurality of particles, update the velocity and the position of each of the plurality of particles based on the pressure and obtain a velocity and a position of each of the plurality of particles at an n+1$^{th}$ time step in combination with the intermediate velocity and the position obtained by the correcting module, search for a particle bulk according to PMS correction to acquire center of gravity (CG) information of the particle bulk, and update a velocity and a position of each particle in the particle bulk according to a calculated velocity and a calculated angular velocity of the particle bulk, so as to complete calculation at each time step in turn, thereby generating real-time melt fragmentation data of the sodium-cooled fast reactor for evaluation of fragmentation characteristics of melts in the sodium-cooled fast reactor.

To make the objects, technical solutions and advantages of the embodiments of the present disclosure clearer, the technical solutions of the present disclosure will be clearly and completely described below with reference to the accompanying drawings. It is clear that the embodiments described herein are merely some embodiments of the present disclosure. Typically, the components of embodiments described and shown in the accompanying drawings herein can be arranged and designed in a variety of different configurations. Accordingly, the following detailed description of embodiments of the present disclosure provided in the accompanying drawings is not intended to limit the protection scope of this application, but rather representing specific embodiments of this application. Based on these embodiments, all other embodiments obtained by one of ordinary skill in the art without creative labor shall fall within the scope of protection of the present disclosure.

Numerical simulations are used to verify the stability and the high accuracy of the algorithm of the aforementioned method based on a high-precision particle method, which simulates the fragmentation process of a melt jet with sodium.

Figure 3:
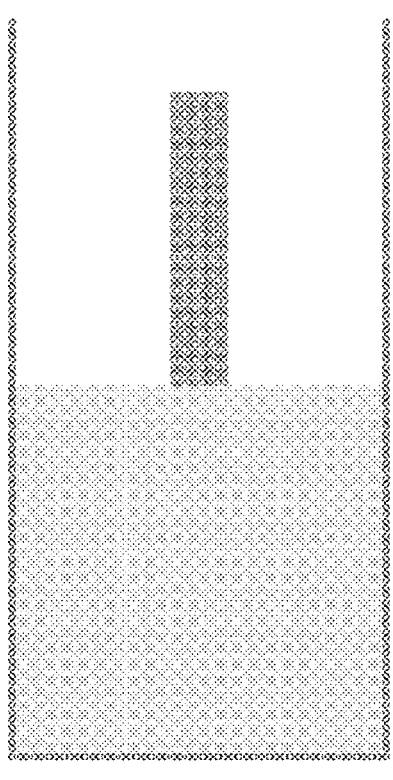
FIG. 3 schematically shows a melt jet model according to an embodiment of the present disclosure.

As shown in FIG. 3, a particle arrangement diagram of a melt jet calculation model is provided, where the initial spacing between the particles is 1×10$^{-3}$ m. The melt material is stainless steel, and the coolant is sodium. At the initial moment, the bottom end of the melt is in contact with the upper surface of the coolant. Due to the large thermal conductivity and heat capacity of sodium, it is assumed in the calculation process that sodium does not suffer gasification. The sodium pool is arranged with 50×50 particles, and the melt is arranged with 8×40 particles. The corresponding size of the sodium pool and the melt are 0.05 m×0.05 m and 0.008 m×0.04 m, respectively. The initial temperature of the melt and is 2000 K, and the initial temperature of the sodium pool is 600 K, which is slightly lower than the temperature of the cold sodium pool in normal operation. The initial speed is 0, and the diameter of the melt is 8 mm.

TABLE 1

| Physical parameters of stainless steel and sodium | | |
|---|---|---|
| Parameters | Stainless steel | Sodium |
| Melting point/K | 1713 | 371 |
| Melting heat/J · kg$^{-1}$ | 269.55 × 10$^3$ | 115 |
| Density/kg · m$^{-3}$ | 7930 | 898 |
| Specific heat/J · (kg · K)$^{-1}$ | 500 | 1360 |
| Heat conductivity coefficient/W · (m · K)$^{-1}$ | 16.0 | 80.6 |
| Dynamic viscosity/Pa · s | 5.88 × 10$^{-3}$ | 0.4131 × 10$^{-3}$ |

The calculation lasts for 2.5 s. The calculating results includes the positional distribution and the temperature distribution of the melt at each moment and the process of solidification of the melt fragments. The total number of melt fragments, the maximum mass of the fragments, and the maximum size of the fragments are monitored during the calculation. The maximum mass of the fragments is expressed by the total number of particles contained in the fragments. For irregular melt fragments, the maximum size is calculated based on the furthest distance of the particles contained in the melt fragments.

Figure 5:
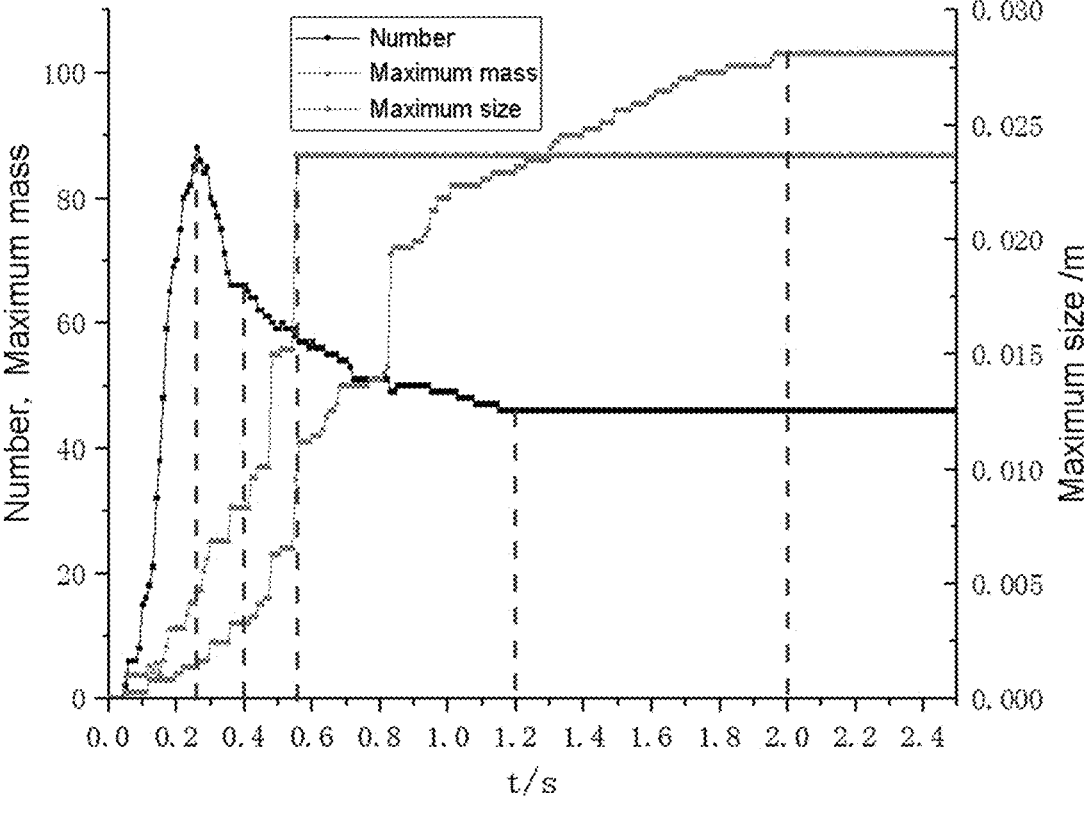
FIG. 5 schematically shows changes in the number of fragments, a maximum fragment mass, and a maximum fragment size over time according to an embodiment of the present disclosure.

For an example with an initial temperature of 2000K, a diameter of 8 mm and an initial velocity of 0, the results at the five moments of 0.05 s, 0.1 s, 0.3 s, 0.8 s, and 2 s are selected for analysis. FIGS. 4a-4c respectively show real-time dynamic plots of melt position distribution, debris formation process, and temperature distribution. FIG. 5 schematically shows changes in the number of fragments, a maximum fragment mass, and a maximum fragment size over time. Hence, the process of melt fragmentation in the sodium-cooled fast reactor can be reproduced and observed.

The present disclosure has certain advantages in technical means for the study of the melt fragmentation process in sodium-cooled fast reactors, and takes the experiment difficulty and cost of core melt fragmentation under real working conditions into account. In real experiments, when a liquid metal is used as a coolant, it is not possible to observe the fragmentation process of a molten material in the metal coolant and to obtain the corresponding data during the process. In the present disclosure, the fragmentation characteristics of the melt into the liquid metal coolant can be analyzed according to the physical parameters of the real reactor core material, and at the same time, it can be investigated from the conditions of different jet speeds, different working temperatures, and different melt sizes and structures. As a result, in the subsequent data processing, it is possible to obtain the morphology changes in the fragmentation process of the melt and the parameters of the generated fragments, which are then analyzed and studied.

In summary, the present disclosure provides a method for evaluating melt fragmentation in a sodium-cooled fast reactor, in which the corresponding model is discretely solved using a high-order accuracy particle method to calculate the melt fragmentation process in the sodium-cooled fast reactor. In this method, the LSMPS method that has high order accuracy for both the gradient model and the Laplace model is used, while the PS technique is used to maintain a more uniform distribution of particles during computation. By combining with the free surface identification technique based on the geometrical method, the Lagrangian particles are more stable during computation, thud obtaining more highly-accurate computational results. Moreover, the equation of state model is introduced to obtain more realistic physical parameters in the calculation process. Combined with the solid-liquid coupling model and the phase transition model, the discretization is carried out with high order accuracy. Finally, the information of melt fragmentation process of the sodium-cooled fast reactor is obtained and analyzed.

It should be understood by those skilled in the art that embodiments of the present application may be provided as methods, systems, or computer program products. Accordingly, the present application may take the form of a fully hardware embodiment, a fully software embodiment, or a combination thereof. Furthermore, the present application may take the form of a computer program product implemented on one or more computer-usable storage media (including, but not limited to, disk memory, CD-ROM, and optical memory) containing computer-usable program codes therein.

The present application is described with reference to flowcharts and/or block diagrams of methods, devices (systems), and computer program products according to embodiments of the present application. It should be understood that each of the processes and/or boxes in the flowchart and/or block diagram, and the combination of processes and/or boxes in the flowchart and/or block diagram, may be implemented by computer program instructions. These computer program instructions may be provided to a processor of a general-purpose computer, a special-purpose computer, an embedded processor, or other programmable data-processing device to produce a machine such that the instructions executed by the processor of the computer or other programmable data-processing device produce a device for carrying out the functions specified in one or more processes in the flowchart and/or one or more boxes in the block diagram.

These computer program instructions may also be stored in a computer-readable memory capable of directing a computer or other programmable data processing device to operate in a particular manner, such that the instructions stored in the computer-readable memory produce an article of manufacture including an instruction device. The instruction device implements a function specified in one or more processes of a flowchart and/or one or more boxes of a block diagram.

These computer program instructions may also be loaded onto a computer or other programmable data processing devices such that a series of operation steps can be performed on the computer or other programmable devices to achieve the computer-implemented processing, such that the instructions can be executed on the computer or other programmable devices to implement the steps specified in one or more processes of a flowchart and/or one or more blocks of a block diagram.

Described above are merely intended to illustrate technical ideas of the present disclosure, and should not be considered as limitations to the present disclosure. It should be noted that any changes, modifications and replacements made on the basis of the technical solutions provided herein without departing from the spirit and scope of the disclosure shall fall within the scope of the disclosure defined by the appended claims.

What is claimed is:

1. A method for monitoring melt fragmentation in a sodium-cooled fast reactor (SFR), comprising:
   (S1) reading and pre-processing information of each of a plurality of particles, wherein the information comprises initial position, velocity, temperature, pressure, phase, and particle bulk number;

(S2) creating a Link-list; determining distribution of the plurality of particles in a grid after the pre-processing in step (S1); searching for neighboring particles with a corresponding cutoff radius, and storing the neighboring particles; determining a free surface; optimizing the distribution of the plurality of particles using an optimized particle-shifting scheme;
   (S3) according to an optimized distribution obtained in step (S2), performing discretization on a temperature discretization operator using a high-order discretization model in combination with a heat transfer and phase transition model; re-calculating temperature, enthalpy and liquid phase volume fraction of each of the plurality of particles in a computational domain according to a heat conduction equation; and updating physical parameters of the plurality of particles according to the temperature and the liquid phase volume fraction in combination with an equation of state (EOS);
   (S4) smoothing density and viscosity of the plurality of particles with updated physical parameters obtained in step (S3);
   (S5) calculating a viscous force of individual particles according to smoothed density and viscosity of the plurality of particles obtained in step (S4) in combination with velocity; calculating a surface tension of the plurality of particles according to an inter-particle free energy model; making explicit correction to the velocity and a position of each of the plurality of particles based on the viscous force, the surface tension and gravity to obtain an intermediate velocity and an intermediate position of each of the plurality of particles at each time step; and
   (S6) solving a pressure Poisson equation according to a least-square moving particle semi-implicit (LSMPS) method to implicitly solve the pressure of each of the plurality of particles; updating the velocity and the position of each of the plurality of particles based on the pressure, and obtaining a velocity and a position of each of the plurality of particles at an $n+1^{th}$ time step in combination with the intermediate velocity and the intermediate position obtained in step (S5); searching for a particle bulk according to Passively Moving Solid (PMS) correction to acquire center-of-gravity (CG) information of the particle bulk; updating a velocity and a position of each particle in the particle bulk according to calculated velocity and calculated angular velocity of the particle bulk, so as to complete calculation at each time step in turn, thereby generating real-time melt fragmentation data of the SFR comprising the number of fragments, a maximum fragment mass and a maximum fragment size; generating a visual dynamic graph of melt fragmentation in real time based on the real-time melt fragmentation data; and monitoring and locating for a user, conditions of the melt fragmentation inside the SFR in real time based on the visual dynamic graph.

2. The method of claim 1, wherein step (S2) comprises: gridding a distribution area of the plurality of particles in a time step; traversing the plurality of particles, and recording a grid location where each particle is located, and serial numbers of particles in each grid; searching for the neighboring particles of each of the plurality of particles in a first circular region, and recording serial numbers of the neighboring particles based on the gridding in a previous time step; searching for neighboring particles of particle i in a second circular region, wherein the second circular region consists of a grid where the particle i is located, and surrounding grids thereof; defining a surrounding area of the particle i as a virtual screen; dividing the virtual screen into $N_v$ quadrants; determining a shadow segment of each of the neighboring particles of the particle i; and calculating the number of shadow segments of individual neighboring particles of the particle i, wherein particles with the number of shadow segments greater than $\frac{1}{6}$ are configured as free surface particles.

3. The method of claim 1, wherein in step (S2), the optimized particle shifting-optimizing scheme is expressed by:

$$\delta \vec{r}_i = -\lambda_{shift}(\Delta l)^2(\nabla D_i - (\vec{n}_i \cdot \nabla D_i)\vec{n}_i) = -\lambda_{shift}(\Delta l)^2(\vec{I} - \vec{n}_i \otimes \vec{n}_i)\nabla D_i;$$

wherein $\delta \vec{r}_i$ represents a corrected displacement; $\lambda_{shift}$ represents a constant parameter; $\Delta l$ represents an initial interparticle distance; D represents a diffusion concentration; and $\vec{n}_i$ represents a corrected unit vector.

4. The method of claim 1, wherein step (S3) is performed through steps of:

(S301) performing the discretization on the temperature discretization operator using the LSMPS method; calculating an enthalpy of each of the plurality of particles in each time step; and calculating a temperature and an enthalpy of each of the plurality of particles in a k+1$^{th}$ time step;

(S302) after calculating the enthalpy of each of the plurality of particles in step (S301), separately calculating the liquid phase volume fraction $\alpha$ and the temperature T of particles of different substances; and (S303) according to enthalpy h and temperature T obtained in each time step, updating the physical parameters of each of the plurality of particles in combination with an equation of state (EOS) model, wherein the EOS model is expressed as:

$$T_{Sm} = T_{Sol} + \frac{T_{Liq} - T_{Sol}}{h_f}(e_{Sm} - e_{Sol});$$

wherein $e_{Sol} < e_{Sm} < e_{Liq}$; $T_{Sm}$ represents a temperature of incompressible particles; $e_{Sol}$ represents a solidus energy; $e_{Sm}$ represents internal energy; and $h_f$ represents enthalpy.

5. The method of claim 4, wherein in step (S301), the temperature $T_i^{k+1}$ and the enthalpy $h_i^{k+1}$ of each of the plurality of particles in the k+1$^{th}$ time step are respectively expressed as:

$$T_i^{k+1} = T_i^k + \frac{\Delta t}{\rho C_P}\frac{2}{n_0}\sum_{j \neq i}\left\{k_{ij}(T_j^k - T_i^k)w_{ij}\frac{[C_3 + C_4]P}{r_{ij}l_0}\right\} \text{ and;}$$

$$h_i^{k+1} = h_i^k + \frac{\Delta t}{\rho}\frac{2}{n_0}\sum_{j \neq i}\left\{k_{ij}(T_j^k - T_i^k)w_{ij}\frac{[C_3 + C_4]P}{r_{ij}l_0}\right\};$$

wherein $T_i^k$ represents a particle temperature within a k$^{th}$ time step; $\Delta t$ represents time step; $\rho$ represents density; $C_P$ represents constant-pressure specific heat; $n_0$ represents number density; $k_{ij}$ represents a thermal-conductivity coefficient; $T_j^k$ represents temperature; $w_{ij}$ represents a kernel function; $r_{ij}$ represents an interparticle distance; $l_0$ represents particle diameter; $C_3 + C_4$ represents a correction matrix in the LSMPS; P represents a relative position vector; and $h_i^k$ is a particle enthalpy within the k$^{th}$ time step.

6. The method of claim 4, wherein in step (S302), the liquid phase volume fraction $\alpha$ and the temperature T of each of the plurality of particles are respectively expressed as:

$$\begin{cases} \alpha_i = 0, h_i \leq h_s \\ \alpha_i = \frac{h_i - h_s}{h_l - h_s}, h_l < h_i < h_s \text{ ; and} \\ \alpha_i = 1, h_i \geq h_l \end{cases}$$

$$\begin{cases} T_i = T_m + \frac{h_i - h_s}{\rho c}, h_i \leq h_s \\ T_i = T_m, h_l < h_i < h_s \\ T_i = T_m + \frac{h_i - h_l}{\rho c}, h_i \geq h_l \end{cases};$$

wherein $\alpha_i$ represents a liquid phase volume fraction of particle i; $h_i$ represents an enthalpy of the particle i; $h_s$ represents a melting enthalpy of a solid particle; $h_l$ represents a solidification enthalpy of a liquid particle; $T_i$ represents a temperature of the particle i; $T_m$ represents a particle melting point; $\rho$ represents density; and c represents specific heat capacity.

7. The method of claim 1, wherein in step (S5), a new momentum conservation equation is expressed as:

$$\frac{D\vec{u}}{Dt} = -\frac{\nabla p}{\rho} + \frac{1}{\rho}\nabla \cdot (\hat{\mu}\nabla \vec{u}) + \vec{g} + \frac{\vec{f}_s}{\rho};$$

wherein $D\vec{u}$ represents a total derivative with respect to velocity; Dt represents a total derivative with respect to time; $\nabla p$ represents a pressure gradient; $\nabla \vec{u}$ represents a velocity gradient; $\vec{g}$ represents gravity; $\vec{f}_s$ represents an additional force other than gravity; and $\rho$ represents density.

8. The method of claim 1, wherein in step (S5), the intermediate velocity and the intermediate position of each of the plurality of particles in each time step are respectively expressed as:

$$\vec{u}^* = \vec{u}^n + \left(\frac{1}{\hat{\rho}}\nabla\hat{\mu}\cdot\nabla\vec{u}^n + \frac{\hat{\mu}}{\hat{\rho}}\nabla^2\vec{u}^n + \vec{g} + \vec{f}^n\right); \text{ and}$$

$$\vec{r}^* = \vec{r}^n + \Delta t\vec{u}^*;$$

wherein $\vec{u}^n$ represents a velocity in an n$^{th}$ time step; $\Delta t$ represents a calculated time step size; $\nabla\hat{\mu}$ represents a viscosity gradient after smoothed; $\nabla\vec{u}^n$ represents a velocity gradient in the n$^{th}$ time step; $\vec{g}$ represents gravity; and $\vec{f}^n$ represents a surface tension in the n$^{th}$ time step.

9. The method of claim 1, wherein in step (S6), the velocity and the position of each of the plurality of particles in the n+1$^{th}$ time step are respectively expressed as:

$$p^{n+1} = p^{**};$$

-continued $$\vec{u}^{n+1} = \vec{u}^* - \Delta t \frac{1}{\hat{\rho}} \nabla p^{n+1};$$

$$\vec{r}^{n+1} = \vec{r}^n + \Delta t \vec{u}^{n+1};$$

$$\vec{r}_i^{n+1} = \vec{r}_i^n + M\left(\vec{r}_i^n - \vec{r}_{c,ii}^n\right); \text{ and}$$

$$\vec{u}_i^{n+1} = \frac{\left(\vec{r}_i^{n+1} - \vec{r}_i^n\right)}{\Delta t};$$

wherein $p^{n+1}$ represents a pressure in the $n+1^{th}$ time step; $\vec{u}^{n+1}$ represents a velocity in the $n+1^{th}$ time step; $\vec{u}^*$ represents the intermediate velocity; $\Delta t$ represents time step; $\hat{\rho}$ represents a smoothed density; $\nabla p^{n+1}$ represents a pressure gradient in the $n+1^{th}$ time step; $\vec{r}^{n+1}$ represents a displacement in the $n+1^{th}$ time step; $\vec{r}^n$ represents a displacement in an $n^{th}$ step; $\vec{r}_i^{n+1}$ represents a displacement of particle i in the $n+1^{th}$ time step; M represents a coordinate transformation matrix; and $\vec{r}_{c,ii}^n$ represents a displacement of a solid block in the $n^{th}$ time step.

10. A computer system, comprising:
one or more processors;
a memory; and
one or more programs;
wherein the one or more programs are stored in the memory, and are configured to cause, when executed by the one or more processors, the computer system to:
(S1) read and pre-process information of each of a plurality of particles, comprising initial position, velocity, temperature, pressure, phase, and particle bulk number;
(S2) create a Link-list; determine distribution of the plurality of particles in a grid after the pre-processing in step (S1); search for neighboring particles with a corresponding cutoff radius, and store the neighboring particles; determining a free surface; optimize the distribution of the plurality of particles using an optimized particle-shifting scheme;
(S3) according to an optimized distribution obtained in step (S2), perform discretization on a temperature discretization operator using a high-order discretization model in combination with a heat transfer and phase transition model; re-calculate temperature, enthalpy and liquid phase volume fraction of each of the plurality of particles in a computational domain according to a heat conduction equation; and update physical parameters of the plurality of particles according to the temperature and the liquid phase volume fraction in combination with an equation of state (EOS);
(S4) smooth density and viscosity of the plurality of particles with updated physical parameters obtained in step (S3);
(S5) calculate a viscous force of individual particles according to smoothed density and viscosity of the plurality of particles obtained in step (S4) in combination with velocity; calculate a surface tension of the plurality of particles according to an inter-particle free energy model; make explicit correction to the velocity and a position of each of the plurality of particles based on the viscous force, the surface tension and gravity to obtain an intermediate velocity and an intermediate position of each of the plurality of particles at each time step; and
(S6) solve a pressure Poisson equation according to a least-square moving particle semi-implicit (LSMPS) method to implicitly solve the pressure of each of the plurality of particles; update the velocity and the position of each of the plurality of particles based on the pressure, and obtain a velocity and a position of each of the plurality of particles at an $n+1^{th}$ time step in combination with the intermediate velocity and the intermediate position obtained in step (S5); search for a particle bulk according to Passively Moving Solid (PMS) correction to acquire center-of-gravity (CG) information of the particle bulk; update a velocity and a position of each particle in the particle bulk according to calculated velocity and calculated angular velocity of the particle bulk, so as to complete calculation at each time step in turn, thereby generating real-time melt fragmentation data of the SFR comprising the number of fragments, a maximum fragment mass and a maximum fragment size; generate a visual dynamic graph of melt fragmentation in real time based on the real-time melt fragmentation data; and monitor and locate for a user, conditions of the melt fragmentation inside the SFR in real time based on the visual dynamic graph.

* * * * *